(12) United States Patent
Bohm et al.

(10) Patent No.: US 7,201,877 B2
(45) Date of Patent: Apr. 10, 2007

(54) DEVICE AND METHOD FOR DETECTING SULFURYL FLUORIDE

(75) Inventors: Holger Bohm, Lübeck (DE); Silke Guga, Lübeck (DE); Andreas Mohrmann, Krummesse (DE); Armin Schulten, Ahrensburg (DE); Bernd Siemensmeyer, Hamberge (DE); Katja Stern, Dissau (DE); Bettina Runge, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 394 days.

(21) Appl. No.: 10/669,323

(22) Filed: Sep. 25, 2003

(65) Prior Publication Data

US 2004/0101967 A1    May 27, 2004

(30) Foreign Application Priority Data

Nov. 23, 2002    (DE) .............................. 102 54 748

(51) Int. Cl.
| | |
|---|---|
| B32B 5/02 | (2006.01) |
| B32B 27/04 | (2006.01) |
| B32B 27/12 | (2006.01) |
| G01N 7/00 | (2006.01) |
| G01N 21/00 | (2006.01) |

(52) U.S. Cl. .............. 422/86; 422/83; 422/94; 422/102; 422/103; 422/104; 436/43; 436/147; 436/119; 436/120; 436/121; 436/123; 436/155; 436/159; 73/1.01; 73/1.02; 73/23.2; 73/23.31

(58) Field of Classification Search ............. 73/1.01, 73/1.02, 23.2, 23.31; 436/43, 147, 119, 120, 436/121, 123, 155, 159; 422/83, 94, 102, 422/103, 104, 86
See application file for complete search history.

(56) References Cited

U.S. PATENT DOCUMENTS 5,000,920 A * 3/1991 Heckmann et al. ........... 422/60

FOREIGN PATENT DOCUMENTS

DE        0 281 938         9/1988

\* cited by examiner

*Primary Examiner*—Brian Sines
(74) *Attorney, Agent, or Firm*—Nixon & Vanderhye P.C.

(57) ABSTRACT

A device for detecting sulfuryl fluoride, in which the gas specimen to be examined is subjected to pyrolysis with ensuing detection of a pyrolysis product, is to be improved for the sake of achieving a mobile, economical structure. To attain this object, in a preliminary tube (1) for pyrolysis, there is a chemical layer (5) of pyrophoric iron, and as an indicator system for the pyrolysis product, a test tube (2) for hydrogen fluoride is used.

6 Claims, 1 Drawing Sheet

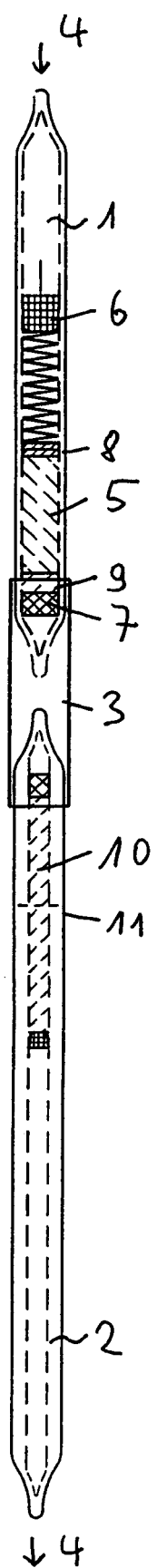

DEVICE AND METHOD FOR DETECTING SULFURYL FLUORIDE

CROSS REFERENCE TO RELATED APPLICATION

This application is based on and incorporates herein by reference German Patent Application No. DE 102 54 748.3-52, filed on Nov. 23, 2002.

BACKGROUND OF THE INVENTION

The invention relates to a device for detecting sulfuryl fluoride and to a method for detecting sulfuryl fluoride.

Sulfuryl fluoride ($SO_2F_2$) is for instance used as a fumigant for killing insects. Sealed rooms in a building are fumigated, using a predetermined action time. The measurement task is on the one hand to trace leaks by way of which the fumigant escapes, and to perform a free measurement after the conclusion of the fumigation.

For detecting sulfuryl fluoride, direct-indicating measuring instruments are known in which $SO_2F_2$ is decomposed in a pyrolysis oven, and the resultant sulfur dioxide is detected with a measurement cell. The detection limit is in a range between 0 and 50 ppm. One such measuring instrument is offered by the company doing business as Ansyco, Analytische Systeme und Komponenten GmbH, with the product designation "GF 1900". Although with the known measuring instrument very low concentrations can be detected, the electrically operated pyrolysis oven requires a heavy battery pack, making the measuring instrument, particularly for leakage measurement, only conditionally portable. The pyrolysis oven furthermore requires major expense for apparatus.

For detecting chlorinated hydrocarbons, it is indeed known from European Patent Disclosure EP 281 938 A1 first to subject the gas specimen to be examined to pyrolysis and then to detect the pyrolysis product, in this case a chlorine compound, with a test tube, but in the known prior art no information can be found on detecting sulfuryl fluoride.

BRIEF DESCRIPTION OF THE INVENTION

The object of the invention is provide a device and a method for mobile, economical detection of sulfuryl fluoride.

This object is attained with a device for detecting sulfuryl fluoride, in which the gas specimen to be examined is subjected to pyrolysis, with ensuing detection of a pyrolysis product, wherein for the pyrolysis, a chemical layer of pyrophoric iron is provided, and that as an indication system for the pyrolysis product, a test tube for hydrogen fluoride is present.

For the method, this object is attained with a method for detecting sulfuryl fluoride, in which the gas specimen to be examined is subjected to pyrolysis, with ensuing detection of a pyrolysis product, wherein the pyrolysis is performed with a chemical layer of pyrophoric iron above 400° Celsius, and the hydrogen fluoride concentration of the pyrolysis product is detected, using a colorimetric test tube.

The advantage of the invention is essentially to perform the pyrolysis of $SO_2F_2$ with a test tube filled with chemicals that is disposed as a preliminary tube on the oncoming-flow side of a commercially available test tube for detecting hydrogen fluoride. The test tube for detecting hydrogen fluoride can be procured for instance from Dräger Safety AG & Co. KGaA, with the product designation "HF 1,5/b-Röhrchen" (HF 1.5/b tube). It is expedient to provide a scale for sulfuryl fluoride, so that a direct readout is possible.

The preliminary tube contains finely divided pyrophoric iron, which because of its large surface area and lattice flaws spontaneously ignites in air and thus attains high temperatures of over 400° Celsius. Pyrophoric iron is produced by the decomposition of iron oxalate; depending upon the iron oxalate quantity used, approximately 25% pyrophoric iron is created, the rest being iron oxide. In the pyrolysis, the pyrophoric iron is converted into solid iron oxide, and sulfuryl fluoride is split into hydrogen fluoride and sulfur dioxide.

Advantageous features of the invention will become apparent from the dependent claims.

Advantageously, the pyrolysis can be markedly improved, and the detection limit of sulfuryl fluoride thus markedly lowered, by adding iron powder or aluminum powder to the pyrophoric iron. This creates more combustible material, and the pyrolysis is optimized in terms of detecting small concentrations of sulfuryl fluoride.

BRIEF DESCRIPTION OF THE DRAWINGS

The sole drawing FIGURE is a schematic view of the device of the invention.

DETAILED DESCRIPTION OF THE INVENTION

One exemplary embodiment of the invention is shown in the drawing and described in further detail below.

The sole drawing FIGURE shows the device of the invention with a preliminary tube 1 and a colorimetric test tube 2 for hydrogen fluoride, of the kind offered by Dräger Safety AG & Co. KGaA under the designation "Fluorwasserstoff 1.5 b, Sachnummer CH 30 301" (Hydrogen fluoride 1.5 b, item number CH 30 301). The tubes 1, 2 are joined together by a hose 3, and the flow direction is represented by arrows 4. The preliminary tube 1 contains a chemical layer 5 between two retaining elements 6, 7 and also contains two quartz glass granulate layers 8, 9. The quartz glass granulate layers 8, 9 serve to prevent the chemical layer 5 from trickling through the retaining elements 6, 7. In the chemical layer 5, iron oxalate and very fine iron powder are mixed together. After the filling, the chemical layer 5 in the preliminary tube 1 is heated to over 400° Celsius. In the process, iron oxalate is converted into pyrophoric iron and iron oxide. The proportion of iron, which reacts strongly exothermally with oxygen when the specimen is taken, is enhanced by the addition of iron powder. Pyrophoric iron is distinguished from normal iron powder by flaws in the lattice. These flaws, together with the large surface area of the finally divided iron, assure that the iron will react so strongly with oxygen that bright red heat results. As the pyrophoric iron is burned off, no combustion gases occur. The colorimetric test tube 2 contains an indicator layer 10 of zirconium quinalizarine and is provided with a scale 11 for the hydrogen fluoride concentration, with a measurement range from 1.5 ppm to 15 ppm.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of using a test tube for detecting hydrogen fluoride as a pyrolysis product and determing sulfuryl fluoride in a gas specimen comprising:

choosing the test tube, the test tube containing pyrophoric iron and an indicator for detecting a pyrolysis product of sulfuryl fluoride and pyrophoric iron, passing the gas specimen through the test tube, detecting, in the test tube, hydrogen fluoride as the pyrolysis product of the gas specimen, and determining, from the detected hydrogen fluoride, the proportion of sulfuryl fluoride in the gas specimen.

2. The method of using a test tube according to claim 1, wherein:

the pyrolysis is performed with a chemical layer of pyrophoric iron above 400° Celsius, and the hydrogen fluoride concentration of the pyrolysis product is detected, using a colorimetric test tube, in order to detect sulfuryl fluoride.

3. The method of claim 2, wherein iron or aluminum powder is added to the chemical layer.

4. A device for detecting sulfuryl fluoride in a gas specimen comprising:

a preliminary tube containing a chemical layer of pyrophoric iron, a colorimetric test tube containing an indicator layer having an indicator for hydrogen fluoride and a scale for hydrogen fluoride concentration, and a connection means for joining the preliminary tube and the colorimetric test tube.

5. A device according to claim 4 wherein the connection means comprises a hose.

6. The device of claim 4, wherein the preliminary tube additionally contains iron or aluminum powder.

* * * * *